United States Patent
Zeccardo et al.

(10) Patent No.: US 10,179,101 B2
(45) Date of Patent: Jan. 15, 2019

(54) PHARMACEUTICAL COMPOSITION FOR TOPICAL APPLICATION IN THE AUDITORY CANAL

(71) Applicant: BIO.LO.GA. S.R.L., Conegliano (Treviso) (IT)

(72) Inventors: Ermelinda Zeccardo, Forli (IT); Claudio Vicini, Forli (IT); Giorgio Panin, Rovigo (IT)

(73) Assignee: BIO.LO.GA. S.R.L., Conegliano (Treviso) (IT)

( * ) Notice: Subject to any disclaimer, the term of this patent is extended or adjusted under 35 U.S.C. 154(b) by 29 days.

(21) Appl. No.: 15/544,766

(22) PCT Filed: Jan. 21, 2016

(86) PCT No.: PCT/EP2016/051215
§ 371 (c)(1),
(2) Date: Jul. 19, 2017

(87) PCT Pub. No.: WO2016/124408
PCT Pub. Date: Aug. 11, 2016

(65) Prior Publication Data
US 2018/0015018 A1    Jan. 18, 2018

(30) Foreign Application Priority Data

Feb. 3, 2015  (IT) .............. MI2015A0139

(51) Int. Cl.
| | | |
|---|---|---|
| *A61K 8/31* | (2006.01) | |
| *A61K 8/67* | (2006.01) | |
| *A61K 9/00* | (2006.01) | |
| *A61K 47/44* | (2017.01) | |
| *A61K 31/355* | (2006.01) | |
| *A61K 9/08* | (2006.01) | |
| *A61Q 19/10* | (2006.01) | |
| *A61K 8/37* | (2006.01) | |
| *A61K 8/81* | (2006.01) | |

(52) U.S. Cl.
CPC ............ *A61K 8/678* (2013.01); *A61K 8/31* (2013.01); *A61K 8/375* (2013.01); *A61K 8/8111* (2013.01); *A61K 9/0046* (2013.01); *A61K 9/08* (2013.01); *A61K 31/355* (2013.01); *A61K 47/44* (2013.01); *A61Q 19/10* (2013.01)

(58) Field of Classification Search
None
See application file for complete search history.

(56) References Cited

FOREIGN PATENT DOCUMENTS

| IT | 1375669 B | 6/2010 |
|---|---|---|
| WO | 9745098 A2 | 12/1997 |
| WO | 2011085155 A2 | 7/2011 |
| WO | 2013065051 A1 | 5/2013 |

OTHER PUBLICATIONS

"Ear Eczema", National Eczema Society, 2015, XP055256430, pp. 1-6.
"Bio-Oil", bio-oil.com, 2002, XP002743518, 1 page.
Oron et al., "Cerumen removal: Comparison of cerumenolytic agents and effect on cognition among the elderly", Archives of Gerontology and Geriatrics, 2010, vol. 52, No. 2, pp. 228-232.
International Search Report and Written Opinion for International Application No. PCT/EP2016/051215 (dated Mar. 16, 2016) (13 pages).

*Primary Examiner* — Necholus Ogden, Jr.
(74) *Attorney, Agent, or Firm* — Lucas & Mercanti, LLP

(57) ABSTRACT

A composition for topical application in the auditory canal is provided. The composition includes 5% to 40% by weight on the total weight of the composition of an ester of vitamin E with a carboxylic acid of formula R—COOH, in which R is an alkyl radical having from 1 to 19 carbon atoms, or an alkenyl or alkynyl radical having from 2 to 19 carbon atoms, and an oily vehicle selected from the group of hydrogenated polyisobutene, hydrogenated polydecene and mixtures of hydrogenated polyisobutene and/or hydrogenated polydecene with hydrogenated polyolefins, in particular hydrogenated $C_6$-$C_{14}$ hydrogenated polyolefins, Caprylic/Capric Triglyceride, Cyclopentasiloxane, and mixtures thereof. The composition can be used to remove earwax from the auditory canal as well as to normalize the epithelium of the auditory canal in cases of friction stress in individuals wearing hearing aids or in individuals using earplugs as hearing protection.

14 Claims, No Drawings

PHARMACEUTICAL COMPOSITION FOR TOPICAL APPLICATION IN THE AUDITORY CANAL

CROSS-REFERENCE TO RELATED APPLICATIONS

This application is a 371 of PCT/EP2016/051215, filed Jan. 21, 2016 which claims the benefit of Italian Application No. MI2015A000139, filed Feb. 3, 2015.

FIELD OF APPLICATION

The present invention relates to the pharmaceutical industry field. Particularly, the invention concerns a composition for topical application in the auditory canal, particularly for use in removing the earwax from the auditory canal and normalizing the epithelium of the auditory canal in cases of friction stress, such as in individuals wearing hearing aids or individuals using earplugs as hearing protection.

PRIOR ART

The earwax forming in the auditory canal results from the production of sebum by sebaceous glands and secretion by slightly modified sweat glands, called ceruminous glands. The earwax, together with the sebum and the secretion of the sweat glands contains a high quantity of keratinocytes peeled away from the stratum corneum of the epithelium covering the auditory canal of the outer ear.

As used herein, by "auditory canal" is meant the outer auditory canal or outer auditory meatus.

An earwax excess remaining in the canal instead of being expelled can cause the formation of the earwax plug.

Therefore, the earwax plug is an ear occlusion due to the accumulation of ceruminous secretion in the outer auditory canal. The "plug" is formed when, due to hygienic or pathological reasons, the earwax is not able to flow outside the auricle. In physiological conditions, indeed, the thin hair that exists in the auditory canal helps the flow of the earwax from the inside to the outside, thus preventing the ceruminous substance from dwelling in the auditory canal.

An earwax plug is formed when the amount of ceruminous secretion produced is extremely abundant, or when its normal outward flow motion is changed. This can be due to multiple reasons, such as seborrheic dermatitis, psoriasis, senescence (ceruminous glands of aged individuals are less trophic and therefore produce dry earwax that finds it harder to slide outwardly), an excessive quantity of water inside the ear, which makes the earwax swell, otitis, hearing aids, which may prevent the earwax from physiologically flowing out, improper ear care carried out using cotton buds.

In order to remove an earwax plug, oily or aqueous solutions are used but with insufficient clinical effectiveness.

Among the commercial products helping with earwax plug removal, Cerulisina® (composed of a dimethylbenzene and almond oil solution) is currently the most used one.

According to the clinical experience of the present inventors, the otoscopy of those patients who are treated in day hospital for earwax plug removal, after they have been using Cerulisina® drops at home in the previous days—after the earwax plug has been removed either by means of irrigation or suction as required—shows severe morphological alterations of the skin covering the auditory canal with reddening, de-epithelialization up to injuries with break in continuity associated with painful symptoms and burning sensation (in a variable percentage based on the period of time elapsed from the plug formation to the removal thereof, computable in about 30% patients, mainly on pediatric and elderly patients who have less perception of the problem).

The patent application WO 2011/85155 describes formulations for removing earwax based on limonene or bile salts or sodium bicarbonate or mixtures thereof, to be administered by instillation or spray, in drops, foam or gel form, in the outer auditory canal.

The patent application WO 2013/65051 describes a pharmaceutical composition in spray particles form, comprising olive squalane and an oily vehicle, which can consist of mineral oil or vegetable oil, particularly light mineral oil and almond oil. The composition can also include an essential oil, a moisturizing oil and/or a disinfectant oil and it is subjected to a pressure of at least 5 bar, to give the particles enough kinetic energy to transform at least part of the solid earwax into liquid earwax.

In the article by Yahav Oron et al., "Cerumen removal: Comparison of cerumenolytic agents and effect on cognition among the elderly", 33-36, ARCHIVES OF GERONTOLOGY AND GERIATRICS, 38, 39 Elsevier, Amsterdam, vol. 52, n. 2, 24 Apr. 2010, pp. 228-232, three products used for the earwax removal are compared:
- CleanEars®, composed of mineral oil, squalane and water mint;
- Auro®, composed of carbamide peroxide and anhydrous glycerin; and
- Cerumol®, composed of peanut oil, chlorobutanol and dichlorobenzene.

In the same article, it is mentioned that several substances have been used for earwax removal, such as water, olive oil, hydrogen peroxide, acetic acid and sodium bicarbonate.

Italian patent no. IT 1 375 669 describes a composition for removing earwax from the auditory canal, comprising 40% to 98% by weight of a mixture of lipids that are fluid at room temperature and 2% to 40% by weight of at least one non-ionic, anionic, amphoteric or cationic emulsifying substance. This composition can further comprise 0.005% to 3.0% by weight of an antioxidant agent, which can be i.a. tocopherol or tocopherol acetate. An example is provided (example 1) of a composition containing, in percentages by weight, ethylhexyl ethylhexanoate 16%, octyldodecanol 30%, C12-C15 alkyl benzoate 20%, ethylhexyl palmitate 20%, polysorbate 85 12.5%, tocopheryl acetate 1% and antimicrobial agent 0.5%.

The "Bio-oil" product, described on the website https://www.bio-oil.com/en/product/ingredients, comprises many ingredients, among which several essential oils and vitamins, including tocopheryl acetate, and an oily vehicle. The indications for use of this product include an application in case of scars, stretch marks, uneven skin tone, ageing skin and dehydrated skin. Nothing is reported in connection with a possible topical application in the auditory canal.

SUMMARY OF THE INVENTION

The object of the present invention is to provide a composition for topical application in the auditory canal.

This object has been achieved by the non-therapeutic use of a composition for topical application in the auditory canal, comprising 5% to 40%, by weight of the total weight of the composition, of an ester of vitamin E with a carboxylic acid of formula R—COOH, in which R is an alkyl radical having 1 to 19 carbon atoms, or an alkenyl or alkynyl radical having 2 to 19 carbon atoms, and an oily vehicle selected from the group consisting of hydrogenated polyisobutene, hydrogenated polydecene and mixtures of hydrogenated polyisobutene and/or hydrogenated polydecene with hydrogenated polyolefins, in particular hydrogenated $C_6$-$C_{14}$ hydrogenated polyolefins, Caprylic/Capric Triglyceride, Cyclopentasiloxane, and mixtures thereof.

According to an aspect of the present invention, this composition is intended for use in cleaning the auditory canal.

According to another aspect of the present invention, this composition is for use in the removal of the earwax from the auditory canal.

According to a further aspect of the present invention, this composition is intended for use in the normalization of the auditory canal epithelium in cases of friction stress, such as for example in individuals wearing hearing aids or individuals using earplugs as hearing protection.

Preferably, the above composition does not include any other ingredient in addition to said ester of vitamin E and said oily vehicle.

By vitamin E, d-α-tocopherol, a mixture of the two d and l enantiomers of α-tocopherol, a mixture of other tocopherols (β, γ, δ, ε, ζ, η) or tocotrienols are meant.

Preferably, the above ester is vitamin E acetate, n-propionate or linoleate.

Particularly preferred is the use of vitamin E acetate, particularly alpha-tocopheryl acetate.

Preferably, the composition comprises 10% to 30% by weight of said ester of vitamin E on the total weight of the composition.

Particularly preferred oily vehicles consist of hydrogenated polydecene and caprylic/capric glyceride (Caprylic/Capric Triglyceride).

A particularly preferred composition consists of alpha-tocopheryl acetate and hydrogenated polydecene.

Advantageously, this composition consists of 10-30% alpha-tocopheryl acetate and 70-90% hydrogenated polydecene.

Another particularly preferred composition consists of alpha-tocopheryl acetate and caprylic/capric glyceride (Caprylic/Capric Triglyceride).

Advantageously, this composition consists of 10-30% alpha-tocopheryl acetate and 70-90% caprylic/capric glyceride (Caprylic/Capric Triglyceride).

Due to its affinity with the cutaneous lipids, the composition used in the present the invention helps to fluidize and dissolve the earwax, thus enabling the natural flowing out from the auditory canal without using cotton buds, and it is suitable to prevent and remove earwax plugs. The composition according to the present invention is particularly useful for those individuals who use hearing aids and make an extended use of earphones.

All percentages given in this application are to be understood, unless otherwise indicated, as percentages by weight of the total weight of the composition.

DETAILED DESCRIPTION

The Applicant has been producing for a number of years a preparation in a spray form based on alpha-tocopheryl acetate, marketed under the name of VEA® ORIS (14% alpha-tocopheryl acetate and 86% hydrogenated polydecene), for application to the oral-pharyngeal mucosa, having an emollient and protective action. The applicant also produces preparations in form of oil, lipophilic gel, spray and cream for skin moisturization and for the adjuvant treatment of skin diseases. Considering the favorable effects observed during the application of the above-mentioned preparations to the skin and to the mucous membranes and considering the easy application of the preparation VEA® ORIS in spray form, the applicant thought to verify if the latter product showed a favorable effect on the auditory canal epithelium as well.

It has actually been observed that the product VEA® ORIS performs a normalization action on the auditory canal epithelium and is also particularly useful for earwax removal, as it will become evident from the experimental results shown herein below.

Clinical Test 1

In the period between September 2013 and June 2014, 30 patients (11 females and 19 males), between 16 and 72 years old (55 years average) showing a perception of occlusion and conductive hearing loss due to the presence of an earwax plug in the auditory canal have been recruited.

The treatment scheme that was used provided for the topical administration of VEA® ORIS spray in the auditory canal according to the following dose: one spray 3 times/day during the 5 days preceding the earwax plug removal.

In all the patients being treated, the earwax plug removal resulted easier than in the case of patients who were previously treated at home with Cerulisina® or other commercial ear drops (for example Debrox®) designated for earwax plugs removal. Upon the otoscopy carried out after ear irrigation, an absolutely normal appearance both as color and trophism of the auditory canal epithelium was observed in all the patients who used VEA® ORIS, without any redness, peeling or abrasions, whereas those patients who used Cerulisina® in the five days preceding the irrigation showed at least redness and in several cases peeling and abrasions, too.

Accordingly, the effect of the application of VEA® ORIS in the auditory canal during the 5 days preceding the removal has been surprising because it allowed to remove the earwax plugs by ear irrigation with a significant reduction in the extraction time while allowing at the same time to guarantee a normal epithelium trophism without having any one of the side effects (redness, burning, even severe de-epithelialization) which very commonly occurred following irrigations carried out in individuals who used other commercial ear products different from VEA® ORIS in the auditory canal during the previous days.

20 of the above-mentioned patients, who presented an anamnesis of recurrent earwax plugs, after the ear irrigation to remove the plug, were suggested to use VEA® ORIS, one spay 3 times a week at least 30 minutes before showering for a 6 months period. In all the individuals during the follow-up visit no new earwax plug formed was observed and the normotrophic appearance of the canal epithelium was observed without any redness or peeling. The product tolerability was of 100%, no individual showed side effects following the repeated and continuous application of VEA® ORIS.

Clinical Test 2

30 patients having chronic eczema of the auditory canal have been asked to apply VEA® ORIS one spray once a day in the evening for 1 month. During the follow-up visit after 30 days, at otoscopy, a complete normalization of the canal epithelium appearance in 70% of the cases and in the remaining 30% a marked reduction in the redness and epithelial peeling was observed. In all the cases, patients reported a decrease in itching and burning sensations up to the disappearance thereof from as early as the second application of VEA® ORIS with remarkable subjective relief.

Clinical Test 3

15 individuals wearing hearing aids, complaining about itching and burning phenomena as well as aural heaviness phenomena resulting from the friction stress generated by the application of the hearing aid and by the continuous daily rubbing, were prescribed the application of one spray of VEA® ORIS every evening, after removing the hearing aid, for 1 month.

After the second application of VEA® ORIS, all the individuals involved reported a better tolerability of the hearing aid, with a marked reduction in the above-mentioned phenomena and such a benefit has continued throughout the period of VEA® ORIS use.

These results suggest that the application of VEA® ORIS can also help in all those working conditions where earplugs are used as hearing protection.

The following formulations were also prepared:

1)

| | |
|---|---|
| Alpha-tocopheryl linoleate | 14% |
| Hydrogenated polydecene | 86% |

2)

| | |
|---|---|
| Alpha-tocopheryl acetate | 10% |
| Hydrogenated polyisobutene | 90% |

3)

| | |
|---|---|
| Alpha-tocopheryl acetate | 14% |
| Caprylic/capric glyceride (Caprylic/Capric Triglyceride) | 86% |

A preliminary testing of the above-mentioned three formulations on three respective groups of five patients, showing a perception of occlusion and conductive hearing loss due to the presence of earwax plug in the auditory canal, in the same experimental conditions as the above-mentioned clinical test 1, gave results comparable to those obtained in the test with the product VEA® ORIS.

The above-mentioned three formulations have also been tested on three respective groups of five patients having chronic eczema of the auditory canal, in the same experimental conditions as the clinical test 2 obtaining results comparable to those obtained in the test with the product VEA® ORIS.

Moreover, a comparative test has been carried out in connection with the ceruminolytic activity of composition used in the present invention in comparison with the composition according to example 1 of IT 1 375 669.

The following formulations were compared:

1) Hydrogenated Polydecene 86 g and Tocopheryl Acetate 14 g;

2) Ethylhexyl Ethylhexanoate 16 g, Octyldodecanol 30 g, C12-C15 Alkyl Benzoate 20 g, Ethylhexyl Palmitate 20 g, Tocopheryl Acetate 1 g, Polysorbate 85 12.5 g, Phenoxyethanol 0.5 g (antimicrobial agent);

3) Caprylic/Capric Triglyceride 86 g, Tocopheryl Acetate 14 g.

Twenty five earwax samples were collected by mechanical removal carried out by physicians specialized in otorhinolaryngology at their doctor's offices.

The samples thus obtained were ground all together in order to obtain a homogeneous mixture.

The above-mentioned three formulations were added to three respective test tubes, each one containing 110 (±1.5) mg of the previously ground earwax, as follows:

Test tube 1: 1.0 g of formulation 1+0.1125 g of earwax;
Test tube 2: 1.0 g of formulation 2+0.1142 g of earwax;
Test tube 3: 1.0 g of formulation 3+0.1146 g of earwax.

A gentle shaking of the three test tubes was carried out 18 hours after their preparation and 5 days after the preparation the still undissolved earwax was extracted from the test tubes. The extracted earwax samples were left to dry until constant weight.

The obtained results are summarized in the following table.

| Test tube identification | Weight of the dry earwax sample at the time of preparation | Weight of the dry earwax sample after 5 days | Difference (in grams) |
|---|---|---|---|
| Test tube no. 1 | 0.1125 | 0.0957 | 0.0168 |
| Test tube no. 2 | 0.1142 | 0.1076 | 0.0066 |
| Test tube no. 3 | 0.1146 | 0.1016 | 0.0130 |

From the results reported in the above table one can deduce that after 5 days:

formulation 1 (contained in test tube no. 1 and consisting of Hydrogenated Polydecene 86 g+Tocopheryl Acetate 14 g) dissolved 0.0168 g of earwax, that is 14.93% of the total earwax;

formulation 2 (contained in test tube no. 2 and according to example 1 of IT 1 375 669) dissolved 0.0066 g of earwax, that is 5.78% of the total earwax;

formulation 3 (contained in test tube no. 3 and consisting of Caprylic/Capric Triglyceride 86 g+Tocopheryl Acetate 14 g) dissolved 0.0130 g of earwax, that is 11.34% of the total earwax.

From the above comparison it clearly appears that the compositions used in the present invention exert a ceruminolytic activity which is significantly higher (substantially double) than that of the formulation known from IT 1 375 669.

The invention claimed is:

1. A method for cleaning an auditory canal of a subject, comprising applying to the auditory canal a composition comprising a) 5% to 40%, by weight of the total weight of the composition, of an ester of vitamin E with a carboxylic acid of formula R—COOH, in which R is an alkyl radical having 1 to 19 carbon atoms, or an alkenyl or alkynyl radical having 2 to 19 carbon atoms, and b) an oily vehicle selected from the group consisting of hydrogenated polyisobutene, hydrogenated polydecene, mixtures of hydrogenated polyisobutene and hydrogenated polydecene with hydrogenated polyolefins, Caprylic/Capric Triglyceride, Cyclopentasiloxane, and mixtures thereof.

2. The method according to claim 1, wherein the cleaning of the auditory canal consists of the removal of earwax from the auditory canal of said subject.

3. The method according to claim 2, wherein said ester of vitamin E is vitamin E acetate, n-propionate or linoleate.

4. The method according to claim 2, wherein said composition comprises 10% to 30%, by weight of said ester of vitamin E based on the total weight of the composition.

5. The method according to claim 2, wherein said oily vehicle consists of hydrogenated polydecene.

6. The method according to claim 5, wherein said ester of vitamin E is alpha-tocopheryl acetate.

7. The method according to claim 6, wherein said composition consists of alpha-tocopheryl acetate and hydrogenated polydecene.

8. The method according to claim 7, wherein said composition consists of 10-30% alpha-tocopheryl acetate and 70-90% hydrogenated polydecene.

9. The method according to claim 2, wherein said oily vehicle consists of caprylic/capric glyceride (Caprylic/Capric Triglyceride).

10. The method according to claim 9, wherein said ester of vitamin E is alpha-tocopheryl acetate.

11. The method according to claim 10, wherein said composition consists of alpha-tocopheryl acetate and caprylic/capric glyceride (Caprylic/Capric Triglyceride).

12. The method according to claim 11, wherein said composition consists of 10-30% alpha-tocopheryl acetate and 70-90% caprylic/capric glyceride (Caprylic/Capric Triglyceride).

13. The method of claim 1, wherein the hydrogenated polyolefin is a $C_6$-$C_{14}$ hydrogenated polyolefin.

14. The method of claim 2, wherein the ester of vitamin E is alpha-tocopheryl acetate.

* * * * *